(12) United States Patent　　Shanmugavel et al.

(10) Patent No.: US 12,575,829 B2
(45) Date of Patent: Mar. 17, 2026

(54) SURGICAL STAPLING APPARATUS WITH ARTICULATION BRAKE ASSEMBLY

(71) Applicant: Covidien LP, Mansfield, MA (US)

(72) Inventors: Logamurugaraj Shanmugavel, Pollachi (IN); Shaik Ahmed Sajid Hussain, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/814,969

(22) Filed: Aug. 26, 2024

(65) Prior Publication Data

US 2025/0099099 A1　　Mar. 27, 2025

Related U.S. Application Data

(60) Provisional application No. 63/585,419, filed on Sep. 26, 2023.

(51) Int. Cl.
　　*A61B 17/072*　　(2006.01)
　　*A61B 17/064*　　(2006.01)
　　*A61B 17/00*　　(2006.01)

(52) U.S. Cl.
　　CPC .... *A61B 17/07207* (2013.01); *A61B 17/0644* (2013.01); *A61B 2017/00473* (2013.01)

(58) Field of Classification Search
　　CPC ...................... A61B 17/07207; A61B 17/0644
　　See application file for complete search history.

(56) References Cited

U.S. PATENT DOCUMENTS

| | | | |
|---|---|---|---|
| 7,784,662 B2 * | 8/2010 | Wales .............. | A61B 17/07207 |
| | | | 227/19 |
| 2010/0193566 A1 * | 8/2010 | Scheib ............. | A61B 17/07207 |
| | | | 227/180.1 |
| 2014/0239040 A1 | 8/2014 | Fanelli et al. | |
| 2015/0374364 A1 * | 12/2015 | Gettinger ......... | A61B 17/07292 |
| | | | 227/175.1 |
| 2017/0224337 A1 | 8/2017 | Williams | |
| 2019/0183503 A1 | 6/2019 | Shelton et al. | |

OTHER PUBLICATIONS

European Search Report for EP application No. EP 24 20 2745 mailed Jan. 27, 2025 (8 pages).

* cited by examiner

*Primary Examiner* — Nathaniel C Chukwurah

(57)　　　　　ABSTRACT

A surgical stapling apparatus includes an elongated shaft assembly defining a longitudinal axis, a tool assembly, a drive beam assembly, and a brake assembly. The tool assembly includes an anvil assembly and a cartridge assembly. The drive beam assembly is selectively advanceable through the tool assembly and positioned to move the tool assembly between an unclamped position and a clamped position. The brake assembly is disposed between the elongated shaft assembly and the tool assembly. The brake assembly includes a movable brake and a fixed brake. The movable brake is positioned to move relative to the fixed brake when the tool assembly moves from the unclamped position to the clamped position. The brake assembly prevents the tool assembly from articulating relative to the longitudinal axis when the moveable brake contacts the fixed brake.

20 Claims, 11 Drawing Sheets

SURGICAL STAPLING APPARATUS WITH ARTICULATION BRAKE ASSEMBLY

CROSS-REFERENCE TO RELATED APPLICATIONS

This application claims the benefit of U.S. Provisional Patent Application Ser. No. 63/585,419, filed Sep. 26, 2023, the entire content of which is incorporated herein by reference.

BACKGROUND

Surgical stapling apparatus configured for endoscopic use are commonly used during surgical procedures to minimize patient trauma and reduce patient recovery times. Typically, endoscopic stapling apparatus include a tool assembly and a drive assembly that is movable in relation to the tool assembly to actuate the tool assembly. The drive assembly includes a knife bar having a cutting blade for cutting tissue. The tool assembly includes anvil and cartridge assemblies that are coupled to each other by a pivot member and movable in relation to each other between unclamped and clamped positions in response to movement of the drive assembly from a retracted position to an advanced position. The cartridge assembly includes a staple cartridge. The staple cartridge includes a cartridge body that supports staples and an actuation sled that is movable through the cartridge body in response to movement of the drive assembly from the retracted position to the advanced position to eject the staples from the cartridge body. The tool assembly is often configured to articulate relative to an elongated shaft of the endoscopic stapling apparatus to access remote locations in a surgical site.

SUMMARY

According to one aspect, this disclosure is directed to a surgical stapling apparatus. The surgical stapling apparatus includes an elongated shaft assembly defining a longitudinal axis and having a proximal end portion and a distal end portion. The surgical stapling apparatus includes a pivot assembly, a tool assembly, a drive beam assembly, and a brake assembly. The pivot assembly is pivotably coupled to the distal end portion of the elongated shaft assembly. The tool assembly is coupled to the pivot assembly. The drive beam assembly is selectively advanceable through the tool assembly and positioned to move the tool assembly between an unclamped position and a clamped position. The brake assembly includes a movable brake and a fixed brake. The movable brake is supported on the pivot assembly and the fixed brake is secured to the elongated shaft assembly. The movable brake is positioned to move relative to the fixed brake when the tool assembly moves from the unclamped position to the clamped position. The brake assembly prevents the tool assembly from articulating relative to the longitudinal axis when the moveable brake contacts the fixed brake.

In aspects, the movable brake may include a first textured surface and the fixed brake may include a second textured surface that is selectively engageable with the first textured surface to prevent relative movement between the first textured surface and the second textured surface.

In aspects, the surgical stapling apparatus may further include a spring supported on the pivot assembly. The spring may be disposed in contact with the moveable brake. The spring may be a leaf spring. The spring may be disposed in contact with a sidewall of the pivot assembly and a sidewall of the movable brake. The spring may be configured to urge the movable brake in a distal direction to maintain the movable brake spaced from the fixed brake by a gap. Movement of the tool assembly from the unclamped position to the clamped position may cause the movable brake to compress the spring. The spring may be movable between an unflexed position and a flexed position. When in the unflexed position, the movable brake may be spaced from the fixed brake, and when in the flexed position, the movable brake may be configured to contact the fixed brake.

In aspects, the surgical stapling apparatus may further include an articulation rod that is coupled to the pivot assembly. The articulation rod may be configured to articulate the pivot assembly as the articulation rod translates between a proximal position and a distal position. When the moveable brake is in contact with the fixed brake, the articulation rod may be prevented from moving in both the proximal direction and the distal direction.

In aspects, the tool assembly may include an abutment surface and the movable brake may include a wedge. The abutment surface of the tool assembly may be configured to contact the wedge to urge the movable brake in a proximal direction toward the fixed brake.

According to another aspect, this disclosure is directed to a surgical stapling apparatus including an elongated shaft assembly defining a longitudinal axis, a tool assembly, a drive beam assembly, and a brake assembly. The tool assembly includes an anvil assembly and a cartridge assembly. The drive beam assembly is selectively advanceable through the tool assembly and positioned to move the tool assembly between an unclamped position and a clamped position. The brake assembly is disposed between the elongated shaft assembly and the tool assembly. The brake assembly includes a movable brake and a fixed brake. The movable brake is positioned to move relative to the fixed brake when the tool assembly moves from the unclamped position to the clamped position. The brake assembly prevents the tool assembly from articulating relative to the longitudinal axis when the moveable brake contacts the fixed brake.

In aspects, the brake assembly further includes a spring, which may be a leaf spring. The spring may be disposed in contact with a sidewall of the movable brake. The spring may be configured to urge the movable brake in a distal direction to maintain the movable brake spaced from the fixed brake by a gap. Movement of the tool assembly from the unclamped position to the clamped position may cause the movable brake to compress the spring. The spring may be movable between an unflexed position and a flexed position. When in the unflexed position, the movable brake may be spaced from the fixed brake, and when in the flexed position, the movable brake maybe configured to contact the fixed brake.

In aspects, the cartridge assembly may include a channel member that supports a staple cartridge. The channel may include an abutment surface and the movable brake may include a wedge. The abutment surface of the channel member may be configured to contact the wedge to urge the movable brake in a proximal direction toward the fixed brake.

According to another aspect, a surgical stapling apparatus includes a tool assembly, an adapter assembly, and a brake assembly. The tool assembly is coupled to the adapter assembly and includes a first jaw member and a second jaw member movable relative to the first jaw member. The adapter assembly defines a longitudinal axis. The brake assembly is supported on a distal end portion of the adapter assembly. The brake assembly includes a movable brake and a fixed brake. The movable brake is positioned to move relative to the fixed brake when the first jaw member moves relative to the second jaw member from a first position to a second position. The brake assembly prevents the tool assembly from articulating relative to the longitudinal axis when the moveable brake and the fixed brake are frictionally engaged.

Other features of the disclosure will be appreciated from the following description.

BRIEF DESCRIPTION OF THE DRAWINGS

The above and other aspects, features, and advantages of this disclosure will be apparent considering the following detailed description when taken in conjunction with the accompanying drawings, which are incorporated in and constitute a part of this specification, wherein.

DETAILED DESCRIPTION

Figure 1:
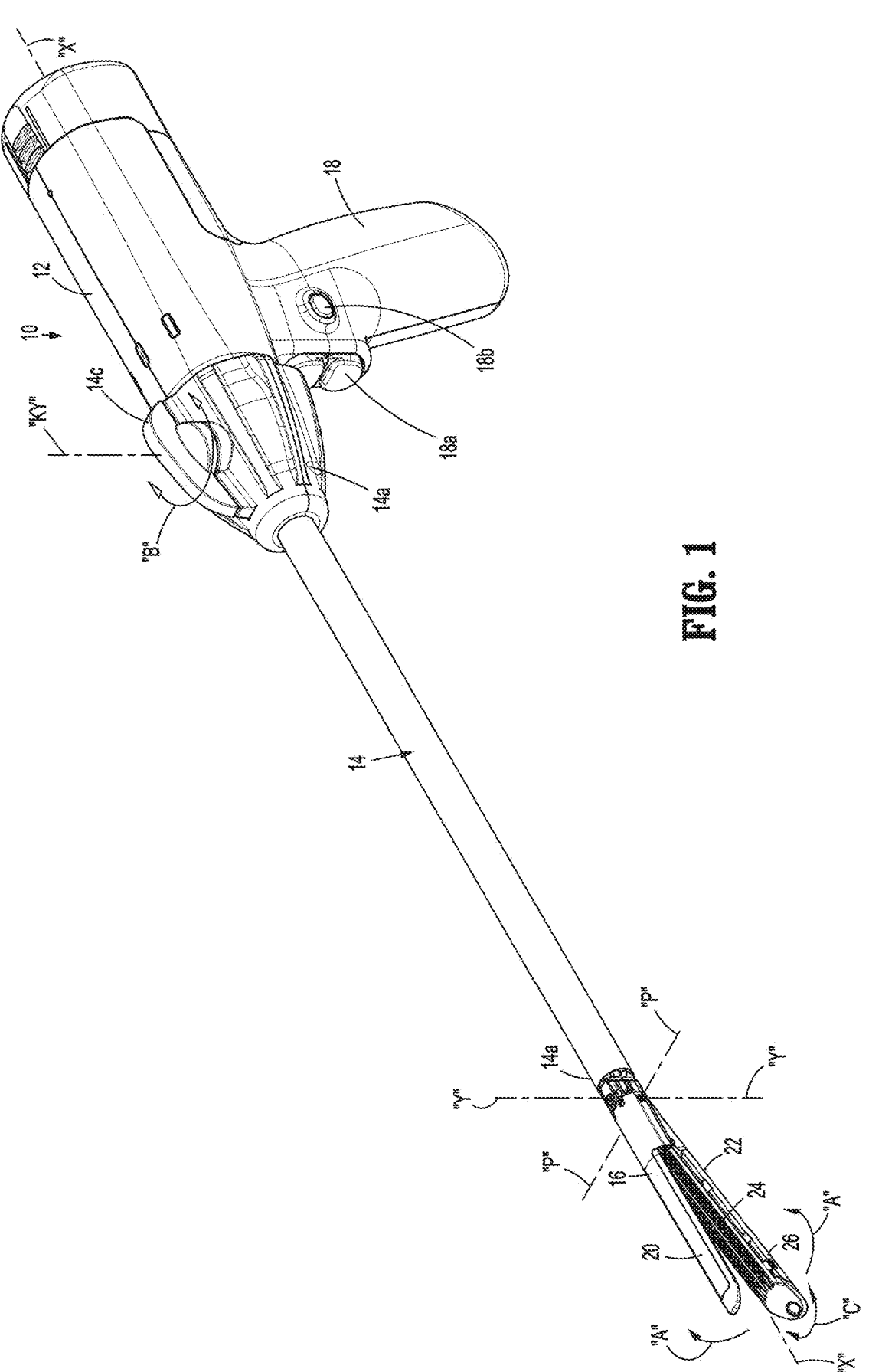
FIG. 1 is a top perspective view of a surgical stapling apparatus, according to aspects of the disclosure, with a tool assembly of the surgical stapling apparatus in an unclamped, pre-fired position.

Aspects of this disclosure will now be described in detail with reference to the drawing figures in which like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," "upper," "lower," and the like, are used to ease description of the aspects and are not intended to have any limiting effect on the ultimate orientation of a structure or any part thereof. Further, the term "clinician" is used generally to refer to medical personnel including doctors, nurses, surgeons, and support personnel.

In the following description, well-known functions or constructions are not described in detail to avoid obscuring this disclosure in unnecessary detail.

Surgical stapling apparatus of this disclosure can be utilized, for example, during laparoscopic surgical procedures that require stapling and/or transecting of tissues and/or organs of various tissue thicknesses. The disclosed surgical stapling apparatus can be configured for single or multi-use surgical stapling.

With reference to FIGS. 1-16, a surgical stapling apparatus, shown generally as stapling apparatus 10, includes a handle assembly 12, an adapter assembly 14, and a tool assembly 16.

Figure 2:
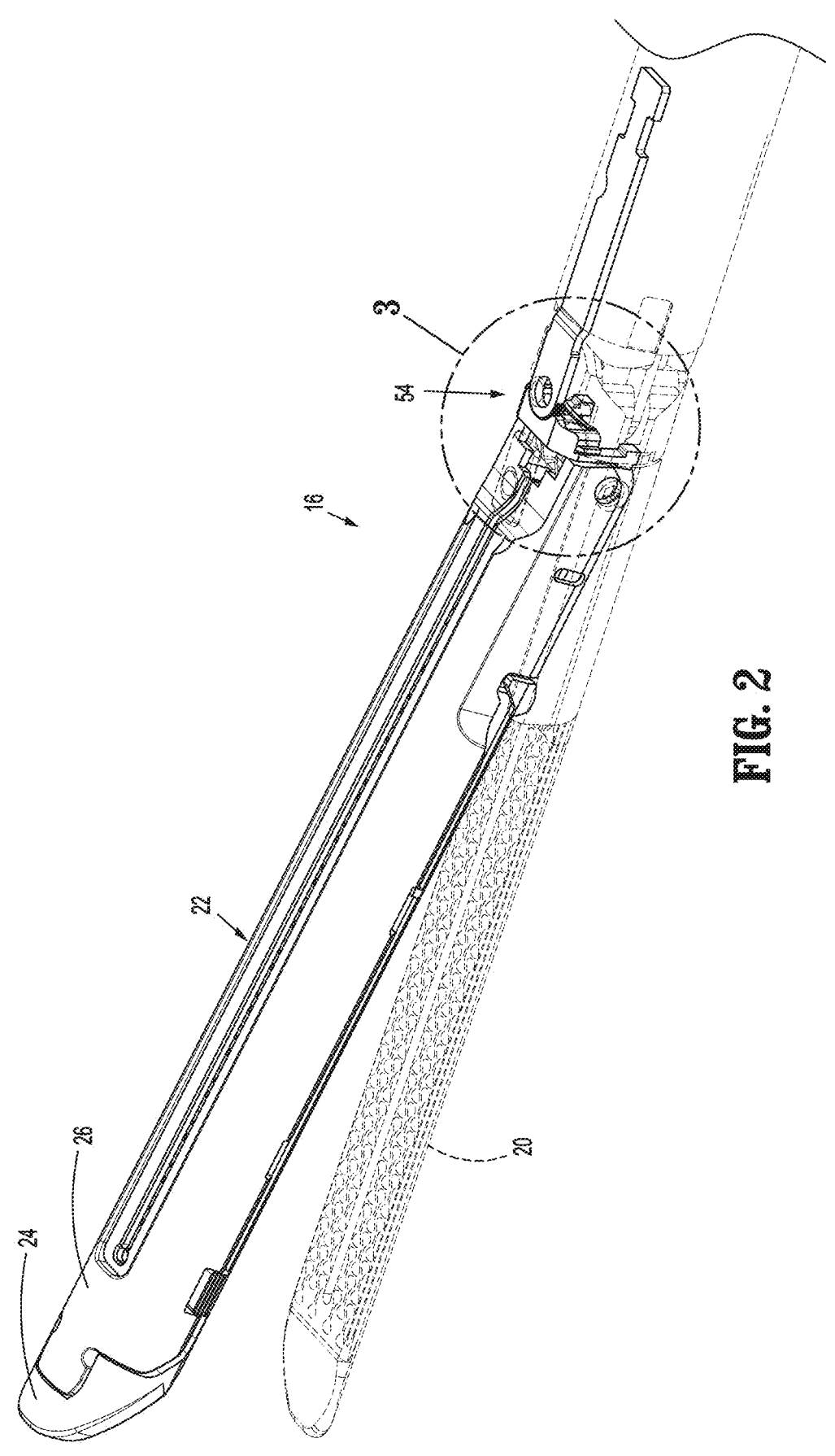
FIG. 2 is an enlarged, bottom perspective view of the tool assembly of FIG. 1 with portions thereof shown in phantom for clarity.

As best seen in FIGS. 1 and 2, the handle assembly 12 of the surgical stapling apparatus 10 is powered and includes a stationary handgrip 18 and an actuation button or buttons 18a, 18b. The actuation buttons 18a, 18b are operable to actuate various functions of the tool assembly 16 via the adapter assembly 14, e.g., clamping of the tool assembly 16, and stapling and cutting of tissue. In certain aspects of the disclosure, the handle assembly 12 may couple to a power source via a cable (not shown) and or support batteries (not shown) that provide power to the handle assembly 12 to operate the stapling apparatus 10. Although the stapling device 10 is illustrated as a powered stapling device, the advantages of this disclosure are suitable for use with other surgical stapling apparatus such as manually powered stapling apparatus and robotically controlled stapling apparatus.

The adapter assembly 14 of surgical stapling apparatus 10 includes a proximal portion 14a and a distal portion 14b. The proximal portion 14a of the adapter assembly 14 is coupled to the handle assembly 12, and the distal portion 14b of the adapter assembly 14 supports the tool assembly 16. The tool assembly 16 is pivotably coupled to the distal portion 14b of the adapter assembly 14, as indicated by arrows "A", to facilitate articulation of the tool assembly 16 in relation to the adapter assembly 14 in clockwise and/or counterclockwise directions about an articulation axis "Y" defined through the distal portion 14b of the adapter assembly 14. Such articulating movement is effectuated in response to rotation of a knob 14c about a knob axis "KY" defined through the proximal portion 14a of the adapter assembly 14, as indicated by arrows "B".

Figure 3:
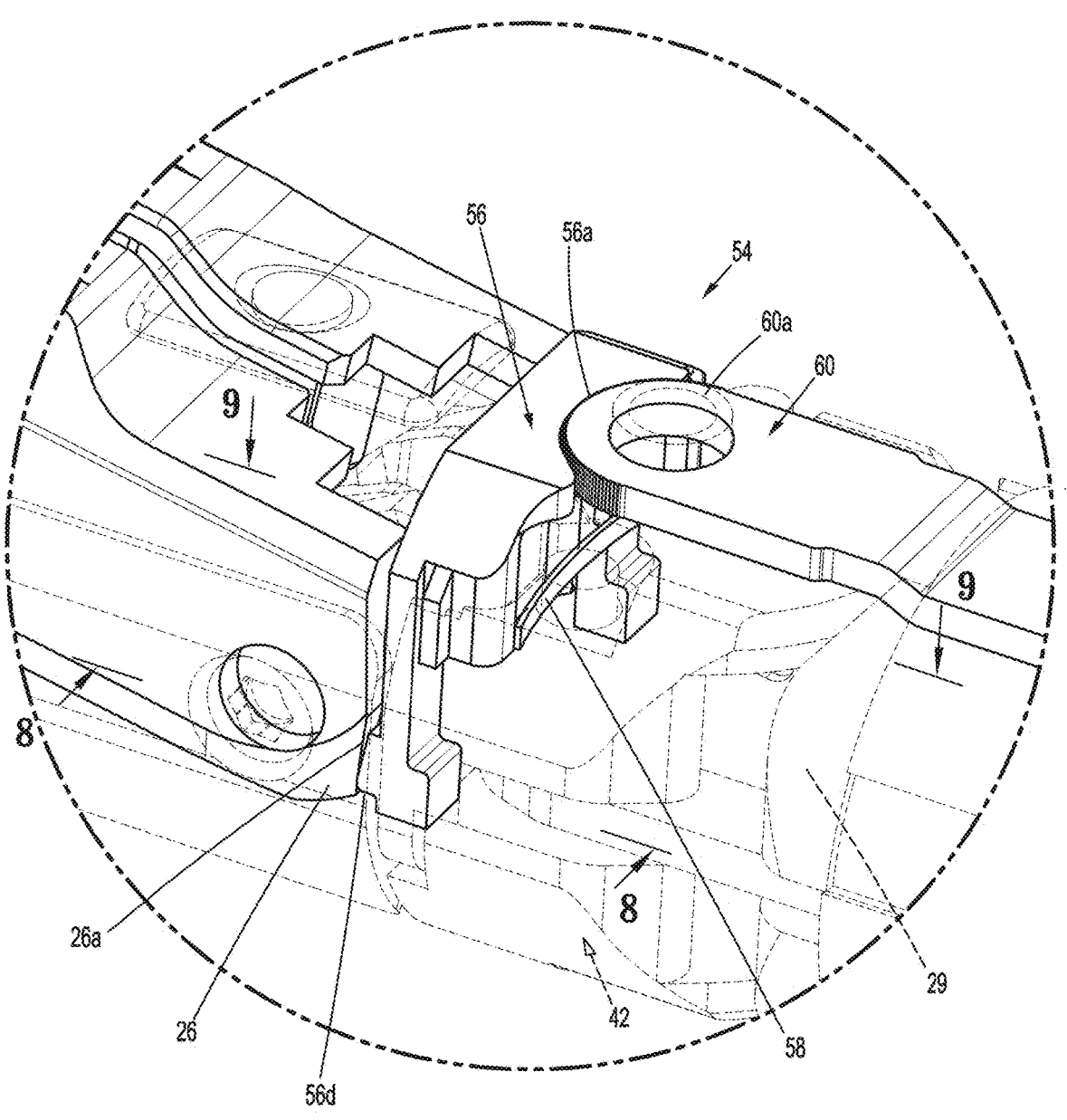
FIG. 3 is an enlarged view of the indicated area of detail shown in FIG. 2.
Figure 4:
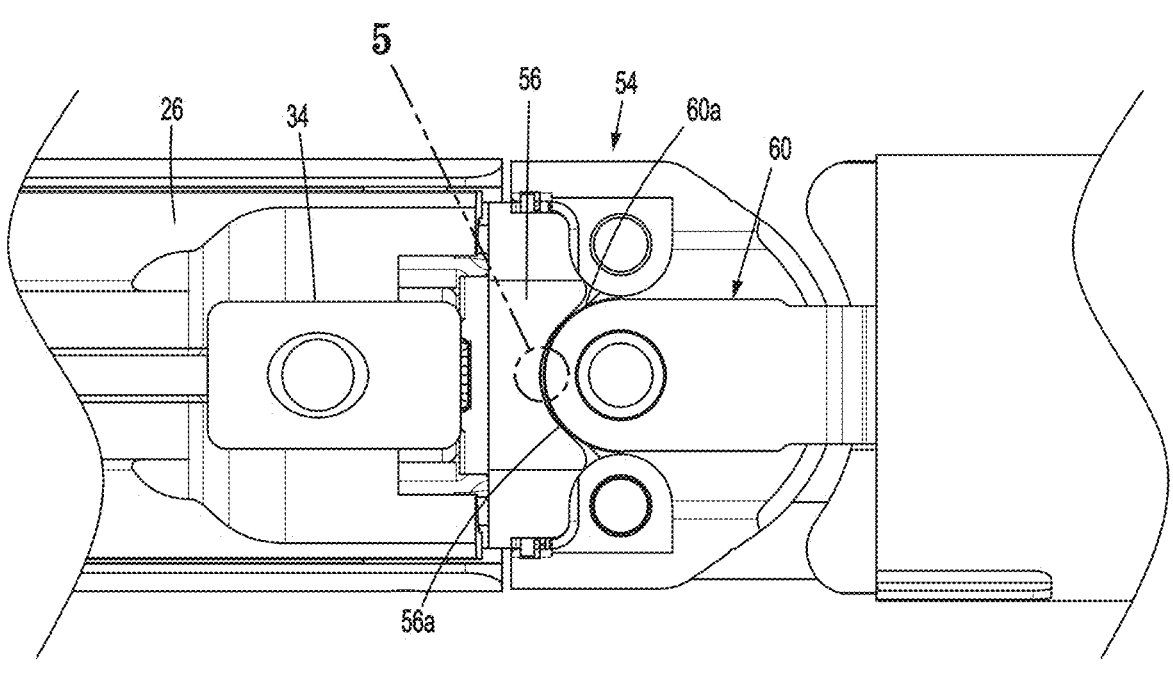
FIG. 4 is a top view of the indicated area of detail shown in FIG. 3.
Figure 5:
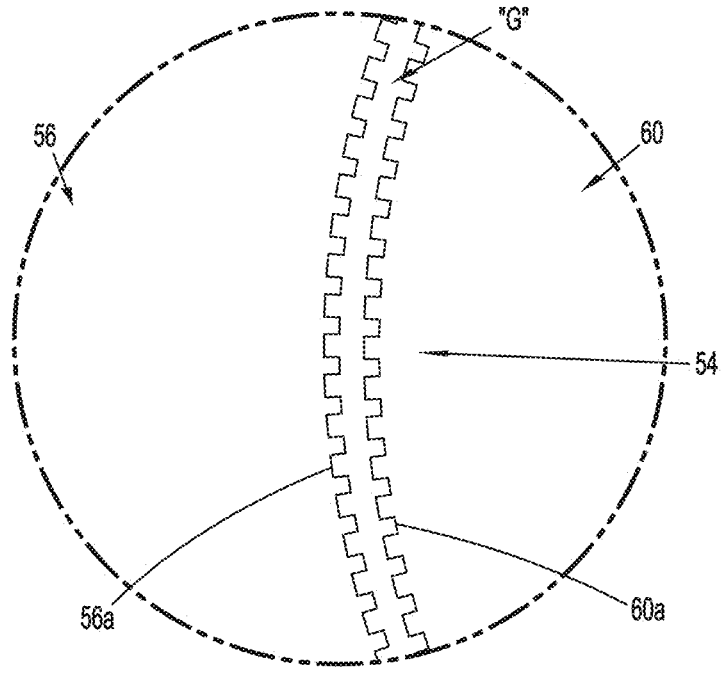
FIG. 5 is an enlarged view of the indicated area of detail shown in FIG. 4.
Figure 6:
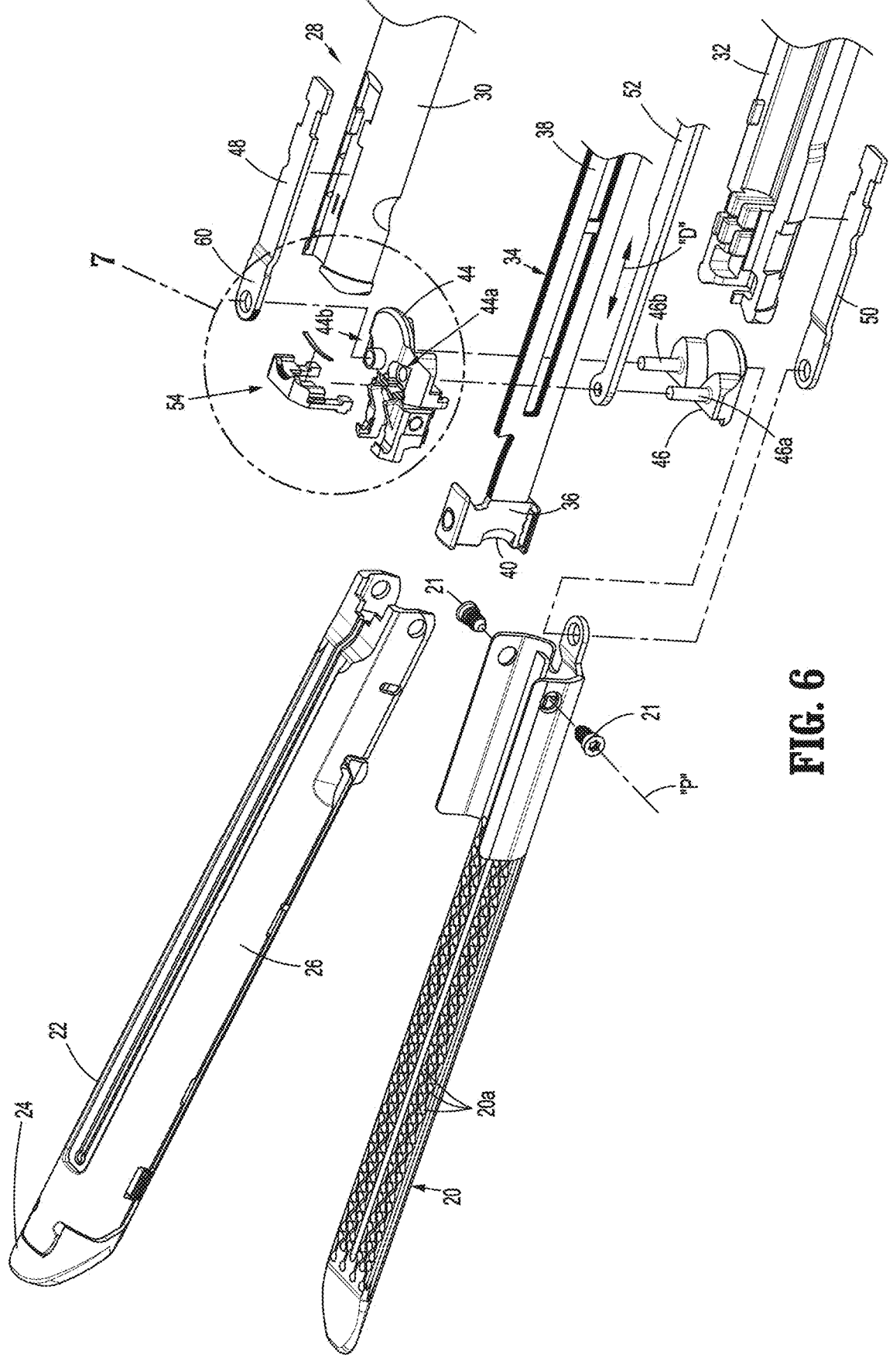
FIG. 6 is a perspective view, with parts separated, of the tool assembly shown in FIG. 2.
Figure 7:
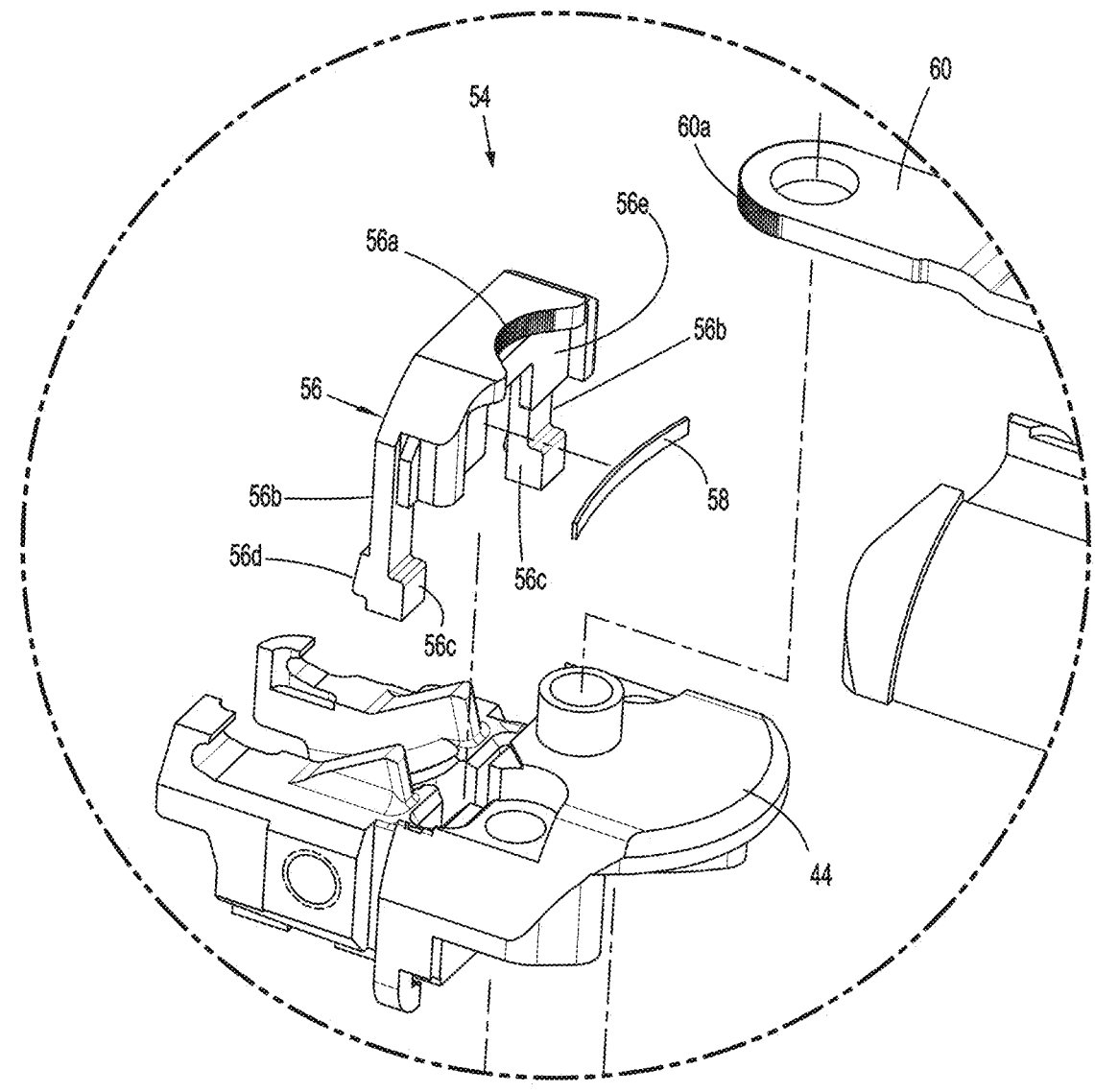
FIG. 7 is an enlarged, perspective view of the indicated area of detail shown in FIG. 6.
Figures 8, 9:
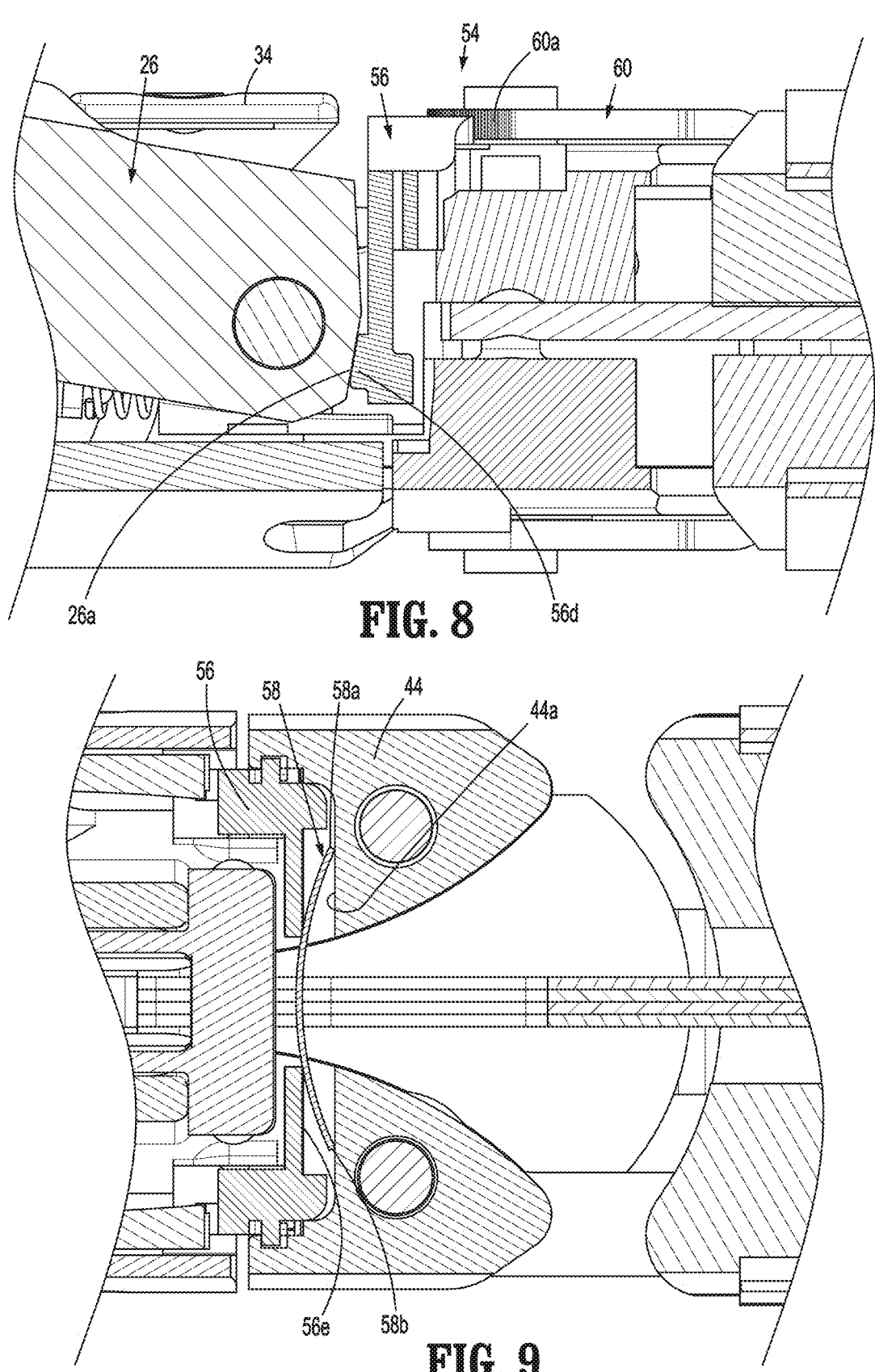
FIGS. 8 and 9 are cross-sectional views as taken along section lines 8-8 and 9-9, respectively of FIG. 2.
Figure 10:
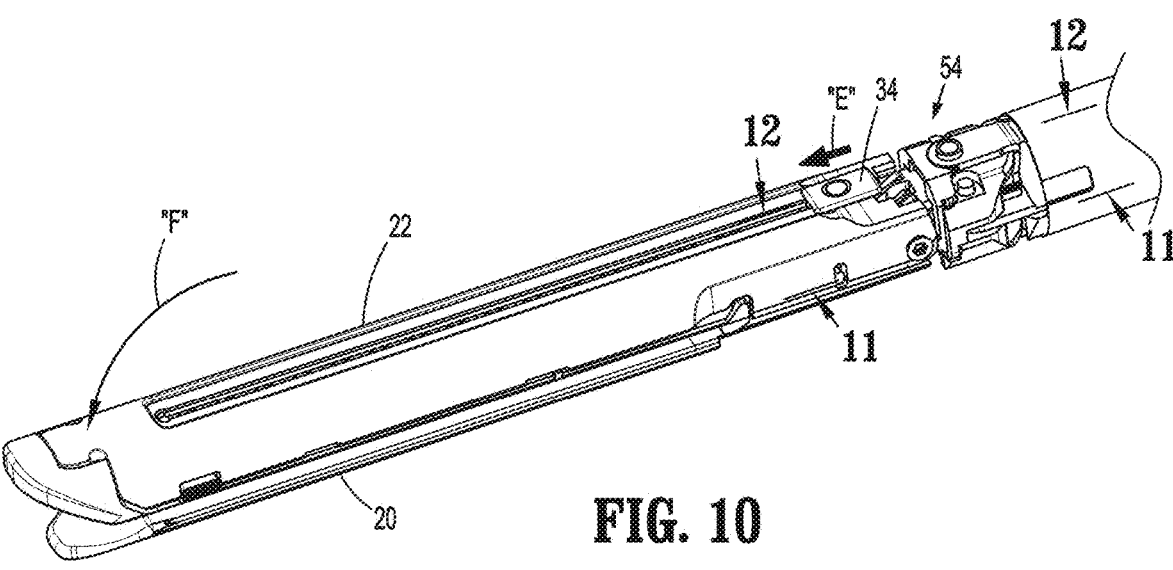
FIG. 10 is a perspective view of the tool assembly in a clamped position.

As best seen in FIGS. 1, 3 and 6, the tool assembly 16 of the surgical stapling apparatus 10 includes a first jaw member in the form of an anvil assembly 20 and second jaw member in the form of a cartridge assembly 22. The anvil and cartridge assemblies 20, 22 are pivotably coupled together by fasteners 21. The cartridge assembly 22 supports a staple cartridge 24 and is pivotably supported in relation to the anvil assembly 20 about a pivot axis "P" defined through the fasteners 21, as indicated by arrows "C", to facilitate movement of the tool assembly 16 between an unclamped position (FIG. 1) and a clamped position (FIG. 10). Alternately and/or additionally, the anvil assembly 20 can be pivotable towards the cartridge assembly 22 to move the tool assembly 16 between the unclamped and clamped positions. The staple cartridge 24 may be removable received within a channel member 26 of the cartridge assembly 22 and is replaceable to facilitate reuse of the stapling apparatus 10.

The adapter assembly 14 includes an elongated shaft assembly 28 defining a longitudinal axis "X" and having a proximal end portion and a distal end portion. The elongated shaft assembly 28 has a shaft housing 29 including a channel-side housing 30 and an anvil-side housing 32. The elongated shaft assembly 28 further supports a movable drive beam assembly 34 having an I-beam 36 supported on a distal end portion of a drive shaft 38. The I-beam 36 is positioned to move the tool assembly 16 from the unclamped position to the clamped position as it translates distally along the tool assembly 16. The drive beam assembly 34 is also positioned to advance distally along the tool assembly 16 to distally advance an actuation sled (not explicitly shown) through the tool assembly 16 and enable staples (not explicitly shown) supported in the staple cartridge 24 to be fired from the staple cartridge 24 for forming the staples against a plurality of rows of staple pockets 20*a* defined in the anvil assembly 20. The I-beam 36 has a blade 40 for cutting tissue clamped by the tool assembly 16 as the drive beam assembly 34 is advanced distally through the tool assembly 16.

The elongated shaft assembly 28 of the adapter assembly 14 further includes a pivot assembly 42 that pivotably couples the tool assembly 16 to the shaft housing 29. The pivot assembly 42 includes a channel-side pivot 44 and an anvil-side pivot 46. The channel-side pivot 44 is pivotably coupled to the channel-side housing 30 of the shaft assembly 29 by a channel-side pivot link 48, and the anvil-side pivot 46 is pivotably coupled to the anvil-side housing 32 by an anvil-side pivot link 50. The anvil-side pivot 46 includes pins 46*a*, 46*b* that are received in apertures 44*a*, 44*b* of the channel-side pivot 44 to couple the anvil-side pivot 46 to the channel-side pivot 44. The elongated shaft assembly 28 further includes an articulation rod 52, which has a proximal end portion that is driven by the handle assembly 12. The articulation rod 52 further includes a distal end portion that is pivotably coupled to pin 46*a* to facilitate pivoting movement of the pivot assembly 42 (e.g., articulating movement relative to the longitudinal axis "X") as the articulation rod 52 translates between proximal and distal positions, as indicated by arrows "D".

The surgical stapling apparatus 10 further includes a brake assembly 54 including a movable brake 56, which is seated on the channel-side pivot 44, a spring 58 (e.g., a leaf spring) supported on the channel-side pivot 44 and disposed in abutment with the movable brake 56, and a fixed brake 60 supported on a distal end portion of the channel-side pivot link 48. The fixed brake 60 includes a distal textured surface 60*a* that is selectively engageable with a proximal textured surface 56*a* of the movable brake 56. The proximal and distal textured surfaces 56*a*, 60*a* of the respective movable and fixed brakes 56, 60 may include, for example, serrations, knurls, protuberances, or any other suitable surface texture that prevents relative sliding movement between surfaces. The spring 58 is movable between an unflexed position (FIG. 9) and a flexed position (FIG. 12) to enable axial movement of the movable brake 56 relative to the fixed brake 60 in response to the pivoting movement of the cartridge assembly 22 relative to the anvil assembly 20. A distal surface of the spring 58 is engaged with a sidewall 56*e* of the movable brake 56 to urge the movable brake 56 in a distal direction for maintaining the proximal textured surface 56*a* of the moveable brake 56 spaced from the distal textured surface 60*a* of the fixed brake 60 by a gap "G" (FIG. 5) when the tool assembly 16 is unclamped and the spring 58 is unflexed. The spring 58 also includes opposite ends 58*a*, 58*b* (see FIGS. 9 and 12) that are positioned in contact with a sidewall 44*a* of the channel-side pivot 44 to provide a counterforce against the spring 58 that enables spring 58 to flex as the movable brake 56 is driven proximally toward the fixed brake 60 in response to pivoting movement of the channel member 26 of the cartridge assembly 22 toward the anvil assembly 20. The proximal textured surface 56*a* of the movable brake 56, which is shown with curved, concave configuration (although other configurations, such as other circular or noncircular configurations are contemplated), is keyed to the distal textured surface 60*a* of the fixed brake 60, which is shown with a curved, convex configuration that complements the proximal textured surface 56*a* of the movable brake 56 (although other configurations are contemplated). In this regard, when the moveable brake 56 and the fixed brake 60 are approximated into frictional engagement, the proximal and distal textured edges 56*a* and 60*a* of the respective moveable and fixed brakes 56, 60 interlock with one another to prevent the pivot assembly 42, and thus the tool assembly 16, from articulating and/or twitching (e.g., an undesired jerking motion of the tool assembly 16) in clockwise and/or counterclockwise directions relative to the longitudinal axis "X" when the surgical stapling apparatus 10 is fired. The movable brake 56 further includes legs 56*b* having feet 56*c* that extend proximally from the legs 56*b* and wedges 56*d* that extend distally from the legs 56*b*. The wedges 56*d* are selectively engageable with a proximal abutment surface 26*a* of the channel member 26 (see FIG. 8) for translating the movable brake 56 relative to the fixed brake 60.

Figure 11:
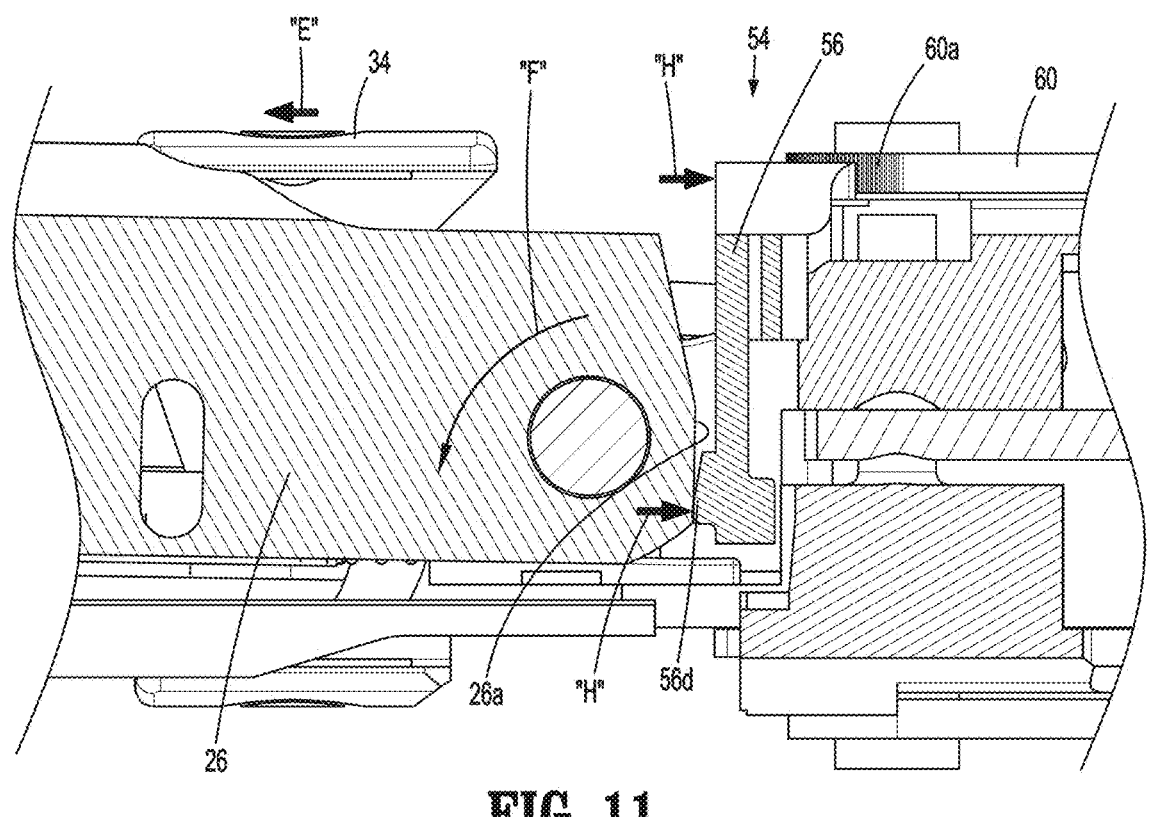
FIGS. 11 and 12 are cross-sectional views as taken along section lines 11-11 and 12-12, respectively of FIG. 10.
Figure 12:
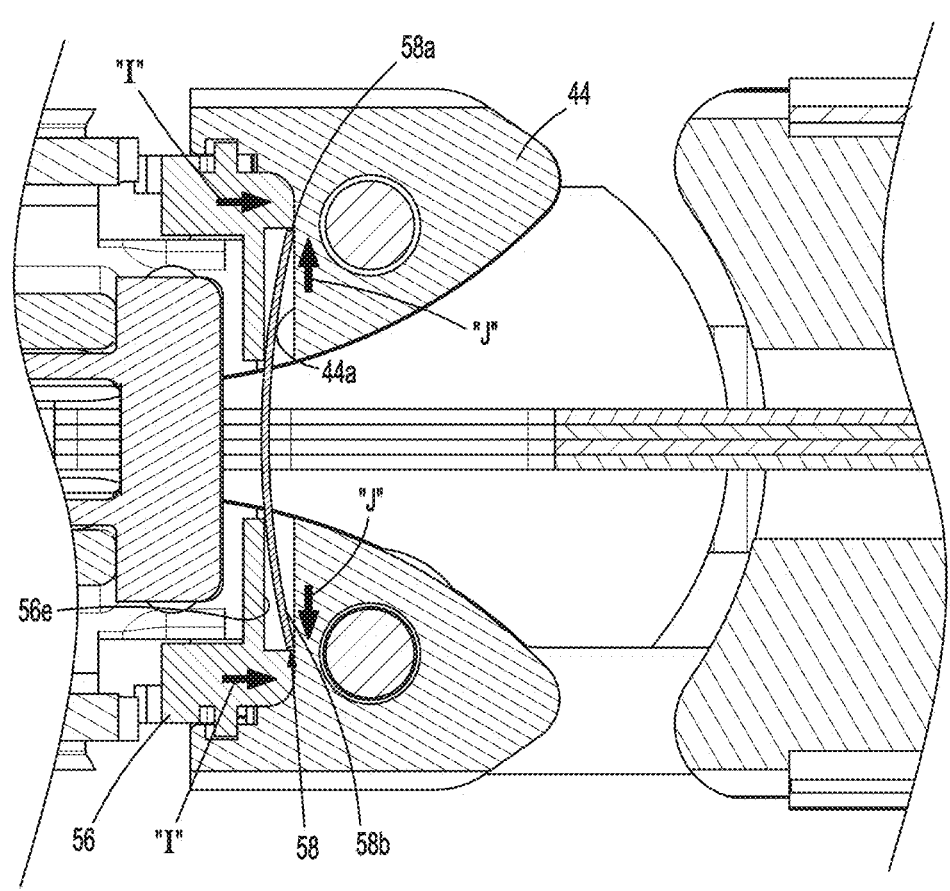
Figure 13:
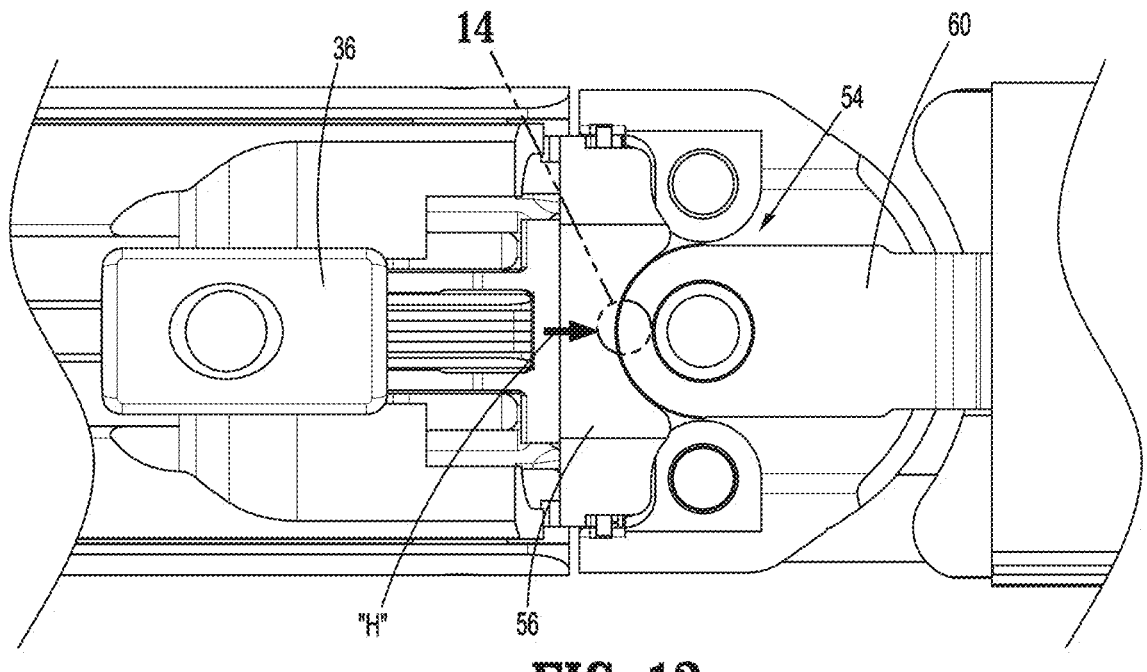
FIG. 13 is a view of FIG. 4 with the tool assembly in the clamped position.
Figure 14:
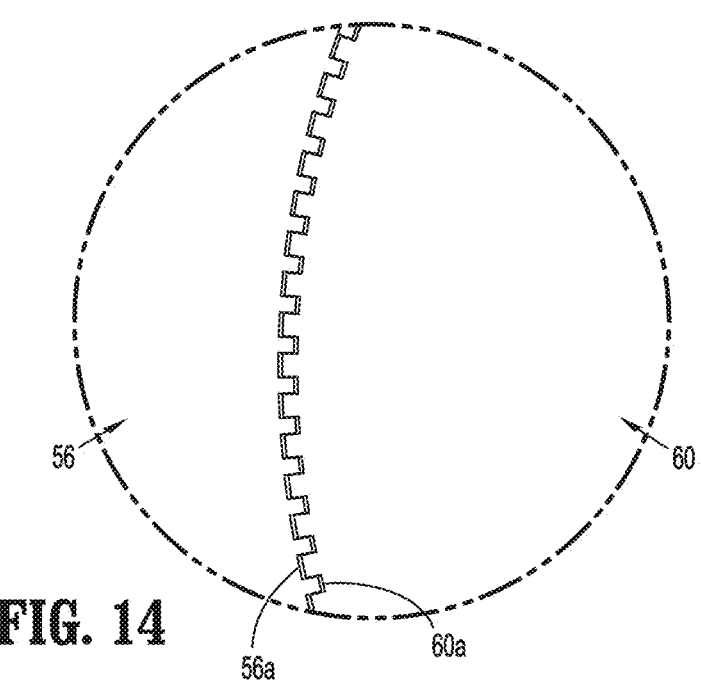
FIG. 14 is an enlarged view of the indicated area of detail shown in FIG. 13.
Figure 15:
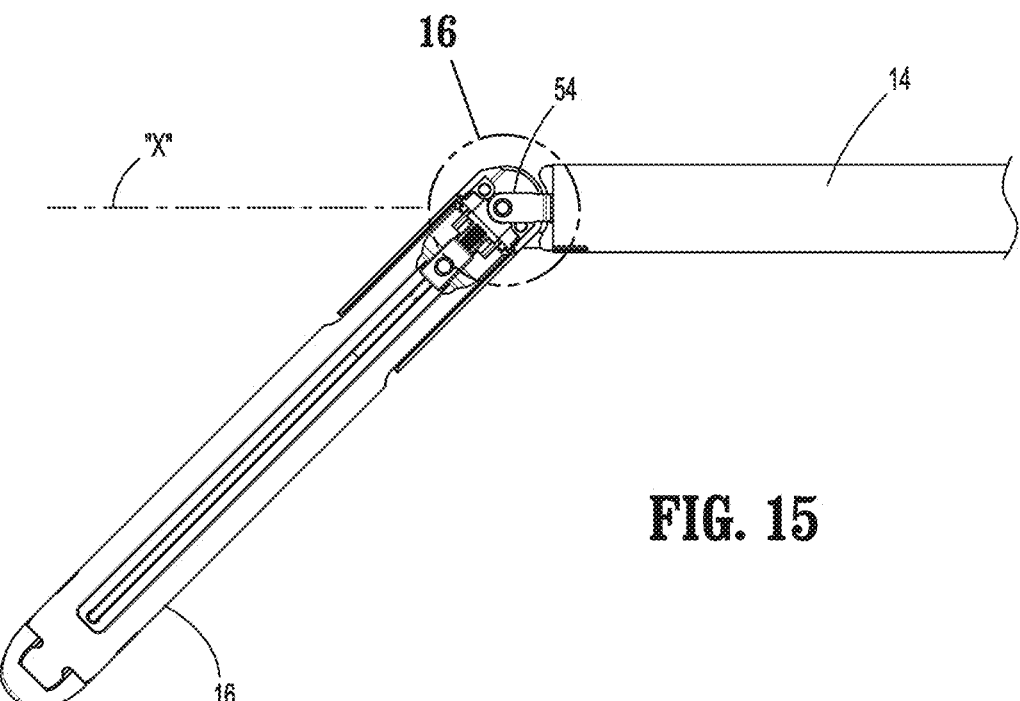
FIG. 15 is a top perspective view illustrating the tool assembly in a clamped and articulated position.
Figure 16:
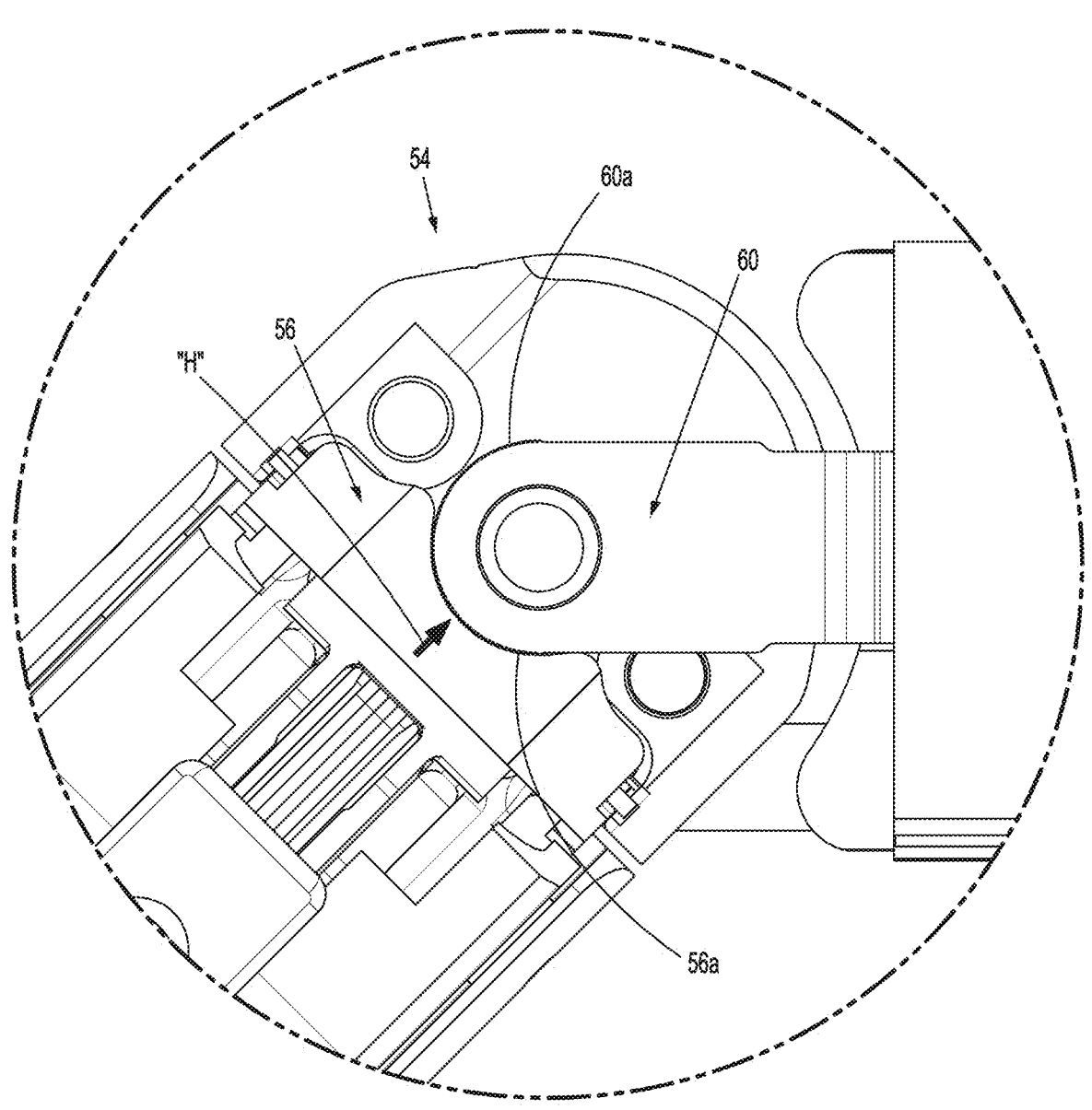
FIG. 16 is an enlarged view of the indicated area of detail shown in FIG. 15.

Once the tool assembly 16 is disposed in a desired position relative to the longitudinal axis "X", whether an unarticulated position as shown in FIGS. 1 and 13 or an articulated position, such as shown in FIGS. 15 and 16, the drive beam assembly 34 is advanced distally along the tool assembly 16, as indicated by arrows "E" in FIGS. 10 and 11, to pivot the cartridge assembly 22 toward the anvil assembly 20, as indicated by arrows "F" in FIGS. 10 and 11, for clamping the tool assembly 16. To prevent the tool assembly 16 from twitching when firing the surgical stapling apparatus 10, such clamping movement causes the proximal abutment surface 26*a* of the channel member 26 to engage the wedges 56*d* of the movable brake 56 and drive the movable brake 56 in a proximal direction toward the fixed brake 60, as indicated by arrows "H" shown in FIGS. 11, 13, and 16. The proximal movement of the movable brake 56 relative to the fixed brake 60 causes the sidewall 56*e* of the movable brake 56 to compress the spring 58, as indicated by arrows "I" shown in FIG. 12, so that the opposite ends 58*a*, 58*b* of the spring 58 push against the sidewall 44*a* of the channel-side pivot 44 and cam radially outward along the sidewall 44*a* of the channel-side pivot 44, as indicated by arrows "J" of FIG. 12, as the spring 58 flexes toward the flexed position. Continued movement of the moveable brake 56 toward the fixed brake 60 causes the proximal and distal textured edges 56*a* and 60*a* of the respective moveable and fixed brakes 56, 60 to frictionally engage, as shown in FIG. 14, so that the tool assembly 16 is prevented from twitching and articulating as the surgical stapling apparatus 10 is fired.

Once the channel member 26 moves toward the unclamped position, the spring 58 urges the movable brake 56 distally away from the fixed brake 60 by a spring force of the spring 58. When the movable and fixed brakes 56, 60 are separated, the tool assembly 16 can be articulated as necessary, for example, to move the surgical stapling apparatus 10 to another position and/or remove the surgical stapling apparatus 10 from a surgical site and/or through an access portal (not shown).

The disclosed subject matter may be further described by reference to the following numbered aspects:

1. A surgical stapling apparatus comprising:
   an elongated shaft assembly defining a longitudinal axis and having a proximal end portion and a distal end portion;

a pivot assembly pivotably coupled to the distal end portion of the elongated shaft assembly;

a tool assembly coupled to the pivot assembly;

a drive beam assembly selectively advanceable through the tool assembly and positioned to move the tool assembly between an unclamped position and a clamped position; and a brake assembly including a movable brake and a fixed brake, the movable brake supported on the pivot assembly and the fixed brake secured to the elongated shaft assembly, the movable brake positioned to move relative to the fixed brake when the tool assembly moves from the unclamped position to the clamped position, wherein the brake assembly prevents the tool assembly from articulating relative to the longitudinal axis when the moveable brake contacts the fixed brake.

2. The surgical stapling apparatus of aspect 1, wherein the movable brake includes a first textured surface, and the fixed brake includes a second textured surface that is selectively engageable with the first textured surface to prevent relative movement between the first textured surface and the second textured surface.

3. The surgical stapling apparatus of aspect 1, further comprising a spring supported on the pivot assembly and disposed in contact with the movable brake.

4. The surgical stapling apparatus of aspect 3, wherein the spring is a leaf spring.

5. The surgical stapling apparatus of aspect 3, wherein the spring is disposed in contact with a sidewall of the pivot assembly and a sidewall of the movable brake.

6. The surgical stapling apparatus of aspect 5, wherein the spring is configured to urge the movable brake in a distal direction to maintain the movable brake spaced from the fixed brake by a gap.

7. The surgical stapling apparatus of aspect 6, wherein movement of the tool assembly from the unclamped position to the clamped position causes the movable brake to compress the spring.

8. The surgical stapling apparatus of aspect 7, wherein the spring is movable between an unflexed position and a flexed position, and wherein in the unflexed position, the movable brake is spaced from the fixed brake, and wherein in the flexed position, the movable brake is configured to contact the fixed brake.

9. The surgical stapling apparatus of aspect 8, further comprising an articulation rod that is coupled to the pivot assembly, the articulation rod configured to articulate the pivot assembly as the articulation rod translates between a proximal position and a distal position, and wherein when the moveable brake is in contact with the fixed brake, the articulation rod is prevented from moving in both the proximal direction and the distal direction.

10. The surgical stapling apparatus of aspect 1, wherein the tool assembly includes an abutment surface, and the movable brake includes a wedge, the abutment surface of the tool assembly configured to contact the wedge to urge the movable brake in a proximal direction toward the fixed brake.

11. A surgical stapling apparatus comprising:

an elongated shaft assembly defining a longitudinal axis;

a tool assembly including an anvil assembly and a cartridge assembly;

a drive beam assembly selectively advanceable through the tool assembly and positioned to move the tool assembly between an unclamped position and a clamped position; and a brake assembly disposed between the elongated shaft assembly and the tool assembly, the brake assembly including a movable brake and a fixed brake, the movable brake positioned to move relative to the fixed brake when the tool assembly moves from the unclamped position to the clamped position, wherein the brake assembly prevents the tool assembly from articulating relative to the longitudinal axis when the moveable brake contacts the fixed brake.

12. The surgical stapling apparatus of aspect 11, wherein the movable brake includes a first textured surface, and the fixed brake includes a second textured surface that is selectively engageable with the first textured surface to prevent relative movement between the first textured surface and the second textured surface.

13. The surgical stapling apparatus of aspect 11, wherein the brake assembly further includes a spring.

14. The surgical stapling apparatus of aspect 13, wherein the spring is a leaf spring.

15. The surgical stapling apparatus of aspect 13, wherein the spring is disposed in contact with a sidewall of the movable brake.

16. The surgical stapling apparatus of aspect 15, wherein the spring is configured to urge the movable brake in a distal direction to maintain the movable brake spaced from the fixed brake by a gap.

17. The surgical stapling apparatus of aspect 16, wherein movement of the tool assembly from the unclamped position to the clamped position causes the movable brake to compress the spring.

18. The surgical stapling apparatus of aspect 17, wherein the spring is movable between an unflexed position and a flexed position, and wherein in the unflexed position, the movable brake is spaced from the fixed brake, and wherein in the flexed position, the movable brake is configured to contact the fixed brake.

19. The surgical stapling apparatus of aspect 11, wherein the cartridge assembly includes a channel member that supports a staple cartridge, and wherein the channel includes an abutment surface, and the movable brake includes a wedge, the abutment surface of the channel member configured to contact the wedge to urge the movable brake in a proximal direction toward the fixed brake.

20. A surgical stapling apparatus comprising:

an adapter assembly defining a longitudinal axis;

a tool assembly coupled to the adapter assembly and including a first jaw member and a second jaw member movable relative to the first jaw member; and a brake assembly supported on a distal end portion of the adapter assembly, the brake assembly including a movable brake and a fixed brake, the movable brake positioned to move relative to the fixed brake when the first jaw member moves relative to the second jaw member from a first position to a second position, wherein the brake assembly prevents the tool assembly from articulating relative to the longitudinal axis when the moveable brake and the fixed brake are frictionally engaged.

The disclosed subject matter may be further described by reference to the following numbered aspects:

21. A surgical stapling apparatus comprising:

an elongated shaft assembly (28) defining a longitudinal axis and having a proximal end portion and a distal end portion;

a pivot assembly (42) pivotably coupled to the distal end portion of the elongated shaft assembly;

a tool assembly (16) coupled to the pivot assembly; and a drive beam assembly (34) selectively advanceable through the tool assembly and positioned to move the tool assembly between an unclamped position and a clamped position;

characterized in that the surgical stapling apparatus includes:

a brake assembly (54) including a movable brake (56) and a fixed brake (60), the movable brake supported on the pivot assembly and the fixed brake secured to the elongated shaft assembly, the movable brake positioned to move relative to the fixed brake when the tool assembly moves from the unclamped position to the clamped position, wherein the brake assembly prevents the tool assembly from articulating relative to the longitudinal axis when the moveable brake contacts the fixed brake.

22. The surgical stapling apparatus of aspect 21, wherein the movable brake includes a first textured surface (56*a*), and the fixed brake includes a second textured surface (60*a*) that is selectively engageable with the first textured surface to prevent relative movement between the first textured surface and the second textured surface.

23. The surgical stapling apparatus of any of the preceding aspects, further characterized by a spring (58) supported on the pivot assembly and disposed in contact with the moveable brake.

24. The surgical stapling apparatus of aspect 23, wherein the spring is a leaf spring.

25. The surgical stapling apparatus of aspects 23 or 24, wherein the spring is disposed in contact with a sidewall (44*a*) of the pivot assembly and a sidewall (56*e*) of the movable brake.

26. The surgical stapling apparatus of any of aspects 23 to 25, wherein the spring is configured to urge the movable brake in a distal direction to maintain the movable brake spaced from the fixed brake by a gap.

27. The surgical stapling apparatus of any of aspects 23 to 26, wherein movement of the tool assembly from the unclamped position to the clamped position causes the movable brake to compress the spring.

28. The surgical stapling apparatus of any of aspects 23 to 27, wherein the spring is movable between an unflexed position and a flexed position, and wherein in the unflexed position, the movable brake is spaced from the fixed brake, and wherein in the flexed position, the movable brake is configured to contact the fixed brake.

29. The surgical stapling apparatus of any of the preceding aspects, further characterized by an articulation rod (52) that is coupled to the pivot assembly, the articulation rod configured to articulate the pivot assembly as the articulation rod translates between a proximal position and a distal position, and wherein when the moveable brake is in contact with the fixed brake, the articulation rod is prevented from moving in both the proximal direction and the distal direction.

30. The surgical stapling apparatus of any of the preceding aspects, wherein the tool assembly includes an abutment surface (26*a*), and the movable brake includes a wedge (56*d*), the abutment surface of the tool assembly configured to contact the wedge to urge the movable brake in a proximal direction toward the fixed brake.

31. The surgical stapling apparatus of any of the preceding aspects, wherein a handle assembly (12) is secured to the proximal end portion of the elongated shaft assembly.

32. The surgical stapling apparatus of any of the preceding aspects, wherein the surgical stapling apparatus is robotically controlled.

33. The surgical stapling apparatus of any of the preceding aspects, wherein the pivot assembly includes a channel-side pivot (44) and an anvil-side pivot (46) that are pinned together.

34. The surgical stapling apparatus of any of the preceding aspects, wherein the drive beam assembly includes an I-beam (36).

35. The surgical stapling apparatus of aspect 34, wherein the I-beam supports a blade (40).

As can be appreciated, securement of any of the components of the presently disclosed apparatus can be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical workstations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary aspects, and that the description, disclosure, and figures should be construed merely as exemplary of aspects. It is to be understood, therefore, that the present disclosure is not limited to the precise aspects described, and that various other changes and modifications may be affected by one skilled in the art without departing from the scope or spirit of the disclosure. Additionally, it is envisioned that the elements and features illustrated or described in connection with one exemplary aspect may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. A surgical stapling apparatus comprising:

an elongated shaft assembly defining a longitudinal axis and having a proximal end portion and a distal end portion;

a pivot assembly pivotably coupled to the distal end portion of the elongated shaft assembly;

a tool assembly coupled to the pivot assembly;

a drive beam assembly selectively advanceable through the tool assembly and positioned to move the tool assembly between an unclamped position and a clamped position; and a brake assembly including a movable brake and a fixed brake, the movable brake supported on the pivot assembly and the fixed brake secured to the elongated shaft assembly, the movable brake positioned to move relative to the fixed brake based at least in part on the tool assembly moving from the unclamped position to the clamped position, wherein the brake assembly prevents the tool assembly from articulating relative to the longitudinal axis when the moveable brake contacts the fixed brake.

2. The surgical stapling apparatus of claim 1, wherein the movable brake includes a first textured surface, and the fixed brake includes a second textured surface that is selectively engageable with the first textured surface to prevent relative movement between the first textured surface and the second textured surface.

3. The surgical stapling apparatus of claim 1, further comprising a spring supported on the pivot assembly and disposed in contact with the movable brake.

4. The surgical stapling apparatus of claim 3, wherein the spring is a leaf spring.

5. The surgical stapling apparatus of claim 3, wherein the spring is disposed in contact with a sidewall of the pivot assembly and a sidewall of the movable brake.

6. The surgical stapling apparatus of claim 5, wherein the spring is configured to urge the movable brake in a distal direction to maintain the movable brake spaced from the fixed brake by a gap.

7. The surgical stapling apparatus of claim 6, wherein movement of the tool assembly from the unclamped position to the clamped position causes the movable brake to compress the spring.

8. The surgical stapling apparatus of claim 7, wherein the spring is movable between an unflexed position and a flexed position, and wherein in the unflexed position, the movable brake is spaced from the fixed brake, and wherein in the flexed position, the movable brake is configured to contact the fixed brake.

9. The surgical stapling apparatus of claim 8, further comprising an articulation rod that is coupled to the pivot assembly, the articulation rod configured to articulate the pivot assembly as the articulation rod translates between a proximal position and a distal position, and wherein when the moveable brake is in contact with the fixed brake, the articulation rod is prevented from moving in both the proximal direction and the distal direction.

10. The surgical stapling apparatus of claim 1, wherein the tool assembly includes an abutment surface, and the movable brake includes a wedge, the abutment surface of the tool assembly configured to contact the wedge to urge the movable brake in a proximal direction toward the fixed brake.

11. A surgical stapling apparatus comprising:

an elongated shaft assembly defining a longitudinal axis;

a tool assembly including an anvil assembly and a cartridge assembly;

a drive beam assembly selectively advanceable through the tool assembly and positioned to move the tool assembly between an unclamped position and a clamped position; and a brake assembly disposed between the elongated shaft assembly and the tool assembly, the brake assembly including a movable brake and a fixed brake, the movable brake positioned to move relative to the fixed brake based at least in part on the tool assembly moving from the unclamped position to the clamped position, wherein the brake assembly prevents the tool assembly from articulating relative to the longitudinal axis when the moveable brake contacts the fixed brake.

12. The surgical stapling apparatus of claim 11, wherein the movable brake includes a first textured surface, and the fixed brake includes a second textured surface that is selectively engageable with the first textured surface to prevent relative movement between the first textured surface and the second textured surface.

13. The surgical stapling apparatus of claim 11, wherein the brake assembly further includes a spring.

14. The surgical stapling apparatus of claim 13, wherein the spring is a leaf spring.

15. The surgical stapling apparatus of claim 13, wherein the spring is disposed in contact with a sidewall of the movable brake.

16. The surgical stapling apparatus of claim 15, wherein the spring is configured to urge the movable brake in a distal direction to maintain the movable brake spaced from the fixed brake by a gap.

17. The surgical stapling apparatus of claim 16, wherein movement of the tool assembly from the unclamped position to the clamped position causes the movable brake to compress the spring.

18. The surgical stapling apparatus of claim 17, wherein the spring is movable between an unflexed position and a flexed position, and wherein in the unflexed position, the movable brake is spaced from the fixed brake, and wherein in the flexed position, the movable brake is configured to contact the fixed brake.

19. The surgical stapling apparatus of claim 11, wherein the cartridge assembly includes a channel member that supports a staple cartridge, and wherein the channel includes an abutment surface, and the movable brake includes a wedge, the abutment surface of the channel member configured to contact the wedge to urge the movable brake in a proximal direction toward the fixed brake.

20. A surgical stapling apparatus comprising:

an adapter assembly defining a longitudinal axis;

a tool assembly coupled to the adapter assembly and including a first jaw member and a second jaw member movable relative to the first jaw member; and a brake assembly supported on a distal end portion of the adapter assembly, the brake assembly including a movable brake and a fixed brake, the movable brake positioned to move relative to the fixed brake based at least in part on the first jaw member moving relative to the second jaw member from a first position to a second position, wherein the brake assembly prevents the tool assembly from articulating relative to the longitudinal axis when the moveable brake and the fixed brake are frictionally engaged.

* * * * *